United States Patent [19]
McHugh

[11] Patent Number: 5,167,952
[45] Date of Patent: Dec. 1, 1992

[54] THERAPEUTIC COMPOSITION FORMULATED AS A DENTAL RINSE THAT STIMULATES PROSTAGLANDIN SYNTHESIS IN THE MOUTH TO PREVENT PLAQUE BUILDUP ON THE TEETH AND PERIODONTAL DISEASE

[76] Inventor: John E. McHugh, 5139 Balboa Blvd., Suite 1, Encino, Calif. 91316

[21] Appl. No.: 771,117

[22] Filed: Oct. 4, 1991

[51] Int. Cl.$^5$ .......................... A61K 7/16; A61K 7/22
[52] U.S. Cl. ...................... 424/49; 514/470; 424/54
[58] Field of Search ............... 424/7.1, 49; 514/470

[56] References Cited

U.S. PATENT DOCUMENTS

| | | | |
|---|---|---|---|
| 4,062,793 | 12/1977 | Schodel | 424/53 |
| 4,428,929 | 1/1984 | Wicheta et al. | 424/49 |
| 4,459,277 | 7/1984 | Kosti | 424/49 |
| 4,459,307 | 7/1984 | McHugh | 424/49 |
| 4,568,534 | 2/1986 | Stier et al. | 424/7.1 |

FOREIGN PATENT DOCUMENTS 106711  2/1927  Austria ................. 424/7.1

*Primary Examiner*—Shep K. Rose

[57] ABSTRACT

This invention relates to novel oral compositions for dental hygiene in the form of a dental rinse and methods of application, effective in the prevention of the formation and buildup of dental plaque on the teeth, causing dental Caries, Calculus and Periodontal disease Gingivitis, and Periodontitis, by stimulating and increasing the rate of Prostaglandin synthesis in the mouth to levels many times higher than that occurring naturally, thereby enhancing and reconstituting the person's Immune System Response and ability to resist bacterial infection so as to effectively control, combat and destroy the natural bacteria in the mouth that cause plaque.

9 Claims, No Drawings

THERAPEUTIC COMPOSITION FORMULATED AS A DENTAL RINSE THAT STIMULATES PROSTAGLANDIN SYNTHESIS IN THE MOUTH TO PREVENT PLAQUE BUILDUP ON THE TEETH AND PERIODONTAL DISEASE

This invention relates to novel oral compositions for dental hygiene in the form of a dental rinse and methods of application, effective in the prevention of the formation and buildup of dental plaque on the teeth, causing dental Caries, Calculus and Periodontal disease Gingivitis and Periodontitis, by stimulating and increasing the rate of Prostaglandin Synthesis in the mouth to levels many times higher than that occurring naturally, thereby enhancing and reconstituting the person's Immune System response and ability to resist bacterial infection, so as to effectively control, combat and destroy the natural bacteria in the mouth that cause plaque.

BACKGROUND OF THE INVENTION

Dental plaque in the form of a film, a combination of bacteria and sticky bacterial products, a by-product of microbial growth is found on the teeth even a few hours after cleaning. Its source is the natural bacteria in the mouth of which more than 300 different species have been identified. When newly formed in small amounts plaque is invisible and relatively harmless. However when it accumulates, plaque is seen as a whitish deposit as the harmful species in the plaque grows. It consists of a mass of microorganisms embedded in a polysaccharide matrix. Plaque adheres firmly to dental surfaces and once the dental plaque buildup is allowed to develope it is difficult to remove.

Periodontal disease Gingivitis and Periodontitis are the most commonly used terms that refer to disease that is caused by the buildup of dental plaque. The Periodontium are the tissues that surround and support the teeth. They include the gums, the gingiva, the bone of the tooth socket, and the periodontal ligament, the thin layer of connective tissue that holds the tooth in its socket and acts as a cushion between tooth and bone.

Inflamation or infection of the gums is called Gingivitis. Infection of the bone is Periodontitis. The plaque that causes Gingivitis is found at or above the gum line and is referred to as supragingival plaque. In time areas of supragingival plaque become covered by swollen gum tissue and spread below the gum line, forming subgingival plaque where harmful bacteria within the plaque proliferate stimulating chronic inflammatory response and the periodontal ligament and bone of the tooth socket are destroyed.

Among the species of bacteria found in the mouth that have been identified as a primary cause of dental plaque buildup and dental caries are Aerobic Gram-Positive Cocci, Streptococcus Mutans and Streptococcus Sanguis. Other bacteria found in the mouth are Aerobic Gram-Negative bacteria Neisseria Sicca found in the nasal pharynx and mouth. Anaerobic Gram-Positive Cocci, PeptococcusMagnus inhabit the mouth as does Anaerobic Gram-Negative Cocci Veillonella Parvula and Gram-Negative Non-Sporeforming Anaerobic Bacilli, Fusobacterium Nucleatum, Bacteroides Fragilis, Leptotrichia Buccalis and Bacteroides Melaninogenicus and many others such as Gram-Positive Non-Sporeforming Anaerobic Bacilli Actinomyces Israelii found in dental Caries, and Calculus. See: The Science of Biology (3d Ed. 1967) pg. 240; Villae, Claude A., Biology (3d Ed. 1957) Pg. 117 et Seq.

Plaque which forms on all parts of the tooth surface is found at the Gingival margin and in dental Calculus. It is this buildup of dental plaque that causes periodontal disease Gingivitis and Periodontitis as well as dental Caries and dental Calculus. Periodontal disease is often described as almost universal, a disease that can or will affect almost everyone. Mouthwashers have proven ineffective in reducing supragingival plaque and plaque related Gingivitis, and there is no evidence that any dental rinse can effect subgingival plaque or Periodontitis. Even the antimicrobial formulation containing Chlorhexidine, a prescription mouthwash shows ineffective reduction of Gingivitis reputed at best to be about 41%. Regular brushing does not prevent plaque buildup for most persons and its removal by a dentist is currently the only safeguard against serious Periodontal disease Gingivitis and Periodontitis.

Researchers are currently studying techniques involving the Immune System function in controlling the types, quantities and location of bacteria in a person's mouth. As plaque consists of about eighty percent live bacteria in a polysaccharide matrix it is necessary that an oral composition to be effective in controlling, eliminating or retarding significantly the growth of bacterial colonies present in plaque, it must have antibacterial properties.

There is therefore a definite need in the Art for an oral hygiene composition with antibacterial properties that stimulates and increases significantly the Immune System Response to control, combat and destroy the plaque causing bacteria found in the mouth and thereby aid in the reduction of Caries formation, development of Calculus and oral diseases Gingivitis and Periodontitis.

It is therefore an object of this invention to provide a fast acting oral hygiene composition with antibacterial properties that will stimulate the Immune System Response to control, combat and destroy the plaque causing bacteria found in the mouth thereby by preventing plaque buildup that results in Caries formation, Calculus and Periodontal disease Gingivitis and Periodontitis.

Phenolphthalein has long been known as one of a group of primary diphenylmethane cathartics. The cathartic effect of the drug Phenolphthalein was reportedly discovered in 1902 and since that time it has been widely employed in laxative formulas. It is also reported that Phenolphthalein is relatively nontoxic. See: Goodman & Gillman Pharmacological Basis of Therapeutics (4th Ed. 1977) Pgs. 1021 and 1022. Phenolphthalein is also used as an indicator in the titration of mineral and organic acids and most alkalis.

Applicant also disclosed methods and uses of Phenolphthalein as an antiviral drug in Treatment of Herpes Simplex Infections and Acne, U.S. Pat. No. 4,256,763 filed Sep. 19, 1978 and issued Mar. 17, 1981; and as an antiviral drug for treating mammalian inflammatory viral infections in U.S. Pat. No. 4,588,744, Filed Jan. 27th, 1981 and issued May 13, 1986. Applicant disclosed methods and uses of Phenolphthalein as an antibacterial drug in U.S. Pat. No. 4,459,307, filed Mar. 24, 1983 and issued Jul. 10, 1984. Applicant disclosed Treatment of Acquired Immunodeficiency Syndrome (AIDS) HTLVlll/LAV infections with Phenolphthalein as an antiviral drug, U.S. Pat. No. 4,970,233 filed Aug. 4, 1987 and issued Nov. 13, 1990.

Phenolphthalein is a potent stimulant of Prostaglandin Biosynthesis. Prostaglandins function primarily as agents of bodily defense in response to injurious stimulus. Prostaglandins a naturally occurring group of substances represent a diverse family of oxygenated derivatives formed from certain polyunsaturated fatty acids. The biosynthesis of Prostaglandins consists of many steps that involve a variety of different enzymes and cofactors.

It is well established that Prostaglandins are important immunoregulators and their role in immune response is currently being investigated. The stimulation of Prostaglandin Synthesis by Phenolphthalein will greatly increase the issue of metabolites to act as local immunoregulators at all physiological and pathological situations in the body.

Immune responses are complex often requiring cooperation between several cell types, genetic and other immune-controlling influences, operating at a number of levels, providing an extremely complex regulatory system that is only beginning to be understood.

Prostaglandins are not normally stored in the tissues but are biosynthesized from fatty acids as and when required on injurious stimulus. Prostaglandins are involved in many physiological and pathological situations. They are involved in the protection of renal function against excessive activity of the pressor hormones, remaining dormant until challanged. The Lungs are involved in the metabolism of Prostaglandins but little is known about the biological activity of the metabolites that are formed. Prostaglandins have potent effects upon Bronchial and Pulmonary Vascular smooth muscle and the lungs have evolved enzyme systems in response to their biological activity.

Prostaglandins are metabolized by tissues to a variety of products in enzymatic reactions, everywhere in the body resulting from injurious stimulus including the nasal pharynx and the mouth. They are synthesized and released from various regions of the body, including for example the Central Nervous System, the Cerebro Spinal Fluid, Coronary Arteries, all layers of the Heart, the Spleen, the Brain, the Kidneys, the Liver, the Nasal Pharynx and the mouth and Semen, a total body defense system activated instantly on localized pathogenic stimulus But like Human Interferon the Prostaglandins at their normal synthesized levels of concentration are not strong enough to inhibit the growth of the invading pathogens. The invading colonies of bacteria found on the teeth and in the oral cavity causing the dental plaque buildup is an example of this condition. What is needed is an excitant to stimulate the rate of Prostaglandin Biosynthesis to levels many times higher than that now occurring naturally. It is believed that Phenolphthalein will provide that needed stimulant.

Prostaglandin Synthesis stimulated by the oral administration of effective dental rinses of Phenolphthalein will cause metabolic formulations, in powerful concentrations at high levels of Prostaglandins effective against among other infections, dental Caries, Calculus and Periodontal disease Gingivitis and Periodontitis.

It is therefore an object of this present invention to provide a method and composition of matter comprising administration of a fast acting oral hygiene composition with antibacterial properties consisting of 800 Mgs. Phenolphthalein dissolved in about Two (2) Milliliters of Triethanolamine and Eight (8) Ozs. of a pharmaceutically acceptable carrier in the form of a dental rinse, administered by taking one (1) tablespoon full and rinsing it around in the mouth on the teeth surfaces and gums, thereby stimulating and increasing the rate of Prostaglandin synthesis in the mouth and oral cavity, and ability to resist bacterial infection, to levels many times higher than that now occurring naturally, and thereby to enhance and reconstitute the Immune System Response to effectively control, combat and destroy dental plaque causing bacterial found in the mouth and prevent plaque buildup that results in Caries formation, Calculus and Periodontal disease Gingivitis and Periodontitis.

It is well known that Phenolphthalein is highly insoluble in water and the high proof alcohol necessary to dissolve the drug has restricted In Vitro and In Vivo clinical studies and testing to an extant that little is known of the drug's antiviral, antibacterial and hormonal stimulating propensities. Inventor herein has discovered that Triethanolamine, an alkalizer, is an especially effective solvent for Phenolphthalein. As little as one milliliter of Triethanolamine will dissolve 400 Mgs. of the drug Phenolphthalein. When this drug is ingested into the human body, less than 15% of the active drug is absorbed into the blood stream. The rest of the drug is excreted in the feces. It is an object of this invention to provide a methodology for rendering the drug Phenolphthalein readily soluble. This solubility not only enhances the drugs ingestibility by and injectability into the human organism, but also allows for high concentrations of the drug in topical applications, carriers and dental rinses.

Preferred embodiment of the dental rinse formulation comprises an alkaline solution with a pH of about 7.5 or above which includes, in a homogeneously admixed liquid alkaline carrier, Pure White Phenolphthalein dissolved in Triethanolamine and additional ingredients Sodium Salicylate or Allantoin as healing agents.

SUMMARY OF THE INVENTION

In accordance with the foregoing objectives this invention provides and discloses a dramatic new change in the current approach to the treatment of Periodontal disease. It provides a fast acting oral hygiene composition dental rinse with antibacterial properties that will stimulate the person's Immune System Response to control, combat and destroy plaque causing bacteria found in the mouth, thereby preventing plaque buildup on the tooth surfaces that result in Caries formation, Calculus and Periodontal disease Gingivitis and Periodontitis.

The invention provides and discloses a novel pharmaceutical composition containing Phenolphthalein dissolved in Triethanolamine and a pharmaceutically acceptable alkaline carrier in the form of a dental rinse, that upon application such as in regular rinsing about on the gums and teeth surfaces, it will stimulate and increase the rate of Prostaglandin synthesis in the mouth and the ability to resist bacterial infection to levels many times higher than that now occurring naturally and thereby enhance and reconstitute the Immune System Response to effectively control combat and destroy bacteria causing dental plaque buildup that results in Caries formation, Calculus and Periodontal disease Gingivitis and Periodontitis.

Phenolphthalein has antibacterial properties and is a potent stimulant of Prostaglandin Synthesis. The factors that determine the rate of Prostaglandin Synthesis are unknown. But this inventor has discovered that Phenolphthalein stimulates Prostaglandin Synthesis in the mouth to levels many times higher than that occurring naturally. It is well established that Prostaglandins are important immunoregulators and their role in the Immune System Response is being thoroughly investigated.

In preferred embodiments of this invention the dental rinse comprises an alkaline solution with a pH of about 7.5 or above, which includes in a liquid alkaline carrier Pure White Phenolphthalein dissolved in Triethanolamine, and additional optional ingredients Sodium Salicylate or Allantoin as healing agents.

It has been found that when the dental rinse of this invention is used daily in a suitable method as for example by placing a tablespoon full of the rinse in the mouth and circulating the rinse thoroughly over the teeth and gums for about thirty seconds a dramatic reduction in plaque formation is noticeable in two or three days. This significant plaque reduction accomplished through the use of the dental rinse indicates that it provides a composition with antibacterial properties that will stimulate the person's Immune System Response to new high levels sufficient to control, combat and destroy the plaque causing bacteria found in the mouth, thereby preventing plaque buildup on the tooth surfaces that result in Caries formation, Calculus and Periodontal disease Gingivitis and Periodontitis.

DETAILED DESCRIPTION

The novel pharmaceutical compositions and methods of administration of the present invention provide for a fast acting oral hygiene composition with antibacterial properties consisting of Pure White Phenolphthalein dissolved in Triethanolamine and a pharmaceutically acceptable alkaline carrier in the form of a dental rinse which when applied in the mouth stimulates and increases the rate of Prostaglandin Synthesis in the mouth and the ability to resist bacterial infection, to levels many times higher than that now occurring naturally and thereby enhanceing and reconstituting the person's Immune System Response to effectively control, combat and destroy bacteria found in the mouth that cause dental plaque buildup that results in Caries formation Calculus and Periodontal disease Gingivitis and Periodontitis.

One formulation of the composition and method of administration of this invention comprises 800 Mgs. of Pure White Phenolphthalein dissolved in about Two (2) Milliliters of Triethanolamine and homogeneously admixed in eight (8) ounces of a pharmaceutically acceptable alkaline carrier in the form of a dental rinse, applied one tablespoon full daily in the mouth and rinsing it around vigorously over the teeth surfaces and gums for thirty seconds, in conjunction with a daily hygiene and tooth brushing regimen.

Prostaglandins a naturally occurring group of substances represent a diverse family of oxygenated derivatives formed from certain polyunsaturated fatty acids, the biosynthesis of Prostaglandins consists of many steps that involve a variety of different enzymes and cofactors.

Prostaglandins are metabolized by tissues to a variety of products in enzymatic reactions everywhere in the body, including the mouth, resulting from injurious stimulus. They are synthesized and released from various regions of the body including for example the Central Nervous System, the Cerebro Spinal Fluid, the Coronary Arteries, all layers of the Heart, the Spleen, the Brain the Kidneys, the Liver, the Semen and the oral cavity and mouth a total defense system activated instantly on localized pathogenic stimulus.

But like Human Interferon the Prostaglandins at their normal synthesized levels of concentration are not strong enough to inhibit the growth of the invading pathogens. This condition applys particularly to the mouth and the enormous numbers of different species of bacteria that invade the oral cavity causing the plaque buildup resulting in dental Caries, Calculus and Periodontal disease Gingivitis and Periodontitis.

What is needed is an excitant to stimulate the rate of Prostaglandin Biosynthesis to levels many times higher than that now occurring naturally which this invention provides as the drug Phenolphthalein.

It is well known that the drup Phenolphthalein is highly insoluble in water and the high proof alcohol necessary to dissolve the drug has restricted clinical studies and testing to an extant that little is known of the drug's antiviral, antibacterial and hormonal stimulating propensities. Inventor herein has discovered that Triethanolamine, an alkalizer is an especially effective solvent for Phenolphthalein. As little as One (1) milliliter of Triethanolamine will dissolve 400 Mgs. of Phenolphthalein. It is an object of this invention to provide a methodology for rendering the drug Phenolphthalein readily soluble. This solubility allows for high concentrations of Phenolphthalein in pharmaceutical carriers in the preparation of dental rinses.

Prostaglandin Synthesis is the most important agent of the normal system of bodily defense naturally existing in the human body, triggered to instant response by every injurious stimulus but lacking in levels of concentration to be effective against such pathogens as the bacteria that invade the mouth.

Oral administration of effective doses of Phenolphthalein dissolved in Triethanolamine formulated in a dental rinse provide the stimulant needed to trigger Prostaglandin Synthesis in powerful enough concentrations at high levels to be effective against the bacteria that cause dental plaque buildup that results in the dental Caries, Calculus and Periodontal disease Gingivitis and Periodontitis.

It has long been established that plaque is made up of about eighty percent live bacteria in a polysaccharide matrix. It is therefore necessary for a dental rinse to be effective to possess significant antibacterial properties in order to retard the growth of the bacterial colonies present in plaque. The levels of concentration of Phenolphthalein employed in embodiments of this dental rinse impart such properties to the formulation.

In preferred embodiments of this dental rinse, formulations comprise an alkaline solution with a pH of 7.5 or above which includes in a liquid carrier Pure White Phenolphthalein dissolved in Triethanolamine and homogeneously admixed in a pharmaceutically acceptable alkaline carrier and homogeneously admixed in a pharmaceutically acceptable alkaline carrier, and effective amounts of substances which promote wound healing such as Sodium Salicylate or Allantoin may be employed. A homogeneous solution of the dental rinse is prepared by thoroughly mixing the active constituent ingredients. For use in a conventional manner, daily dosage of one tablespoon full rinsed vigorously about in the mouth over the teeth surfaces and gums for thirty seconds is recommended.

Examples of the use and success of the rinse are as follows.

Five persons were given the dental rinse and instructed to use it once a day, rinsing a tablespoon full in the mouth vigorously over the teeth surfaces and gums for about thirty seconds, in conjunction with their regular hygiene and tooth brushing regiment. All five persons noticed a dramatic reduction in plaque formation and Gingival inflamation after three days and a significant highly evident clearing of plaque and gum inflamation after five days. This informal test demonstrates that the dental rinse of this invention is an effective agent in the reduction and prevention of plaque buildup and Periodontal disease.

Five other persons were given the dental rinse, after an examination with plaque disclosure tablets. The plaque disclosure tablets contain a red dye which stains plaque but does not stain the plaque free enamel surfaces of the teeth. The percentage of plaque coverage of the teeth surfaces were estimated. Each person was instructed to use the rinse once a day, rinsing a tablespoon full in the mouth vigorously over the teeth and gums for thirty seconds, in conjunction with their regular hygiene and tooth brushing regimen for five days. After the conclusion of the five day test period, all five persons in this informal test of the dental rinse exhibited over 90% reduction in plaque buildup and there was significant reduction in gum inflamation.

These tests demonstrate the ability of the dental rinse of this invention to stimulate the person's immune system response to control, combat and destroy plaque causing bacteria found in the mouth, thereby preventing plaque buildup on the tooth surfaces that result in Caries formation, Calculus and Periodontal disease Gingivitis and periodontitis.

This invention has been described in terms of specific embodiments set forth in detail herein but it should be understood that these are by way of illustration and the invention is not necessarily limited thereto. Modifications and variations will be apparent from the disclosure. and may be resorted to without departing from the spirit of the invention as those of skill in the Art will readily understand. Accordingly such variations and modifications are considered to be within the purview and scope of the invention and the following claims.

What is claimed is:

1. A therapeutic composition with antibacterial properties consisting of Pure White Phenolphthalein dissolved in Triethanolamine an alkalizer which is a solvent therefore, homogeneously admixed in, an alkalizer which is a solvent therefore, homogeneously admixed in a pharmaceutically acceptable alkaline carrier in the form of a dental rinse, which when applied in the mouth stimulates and increases the rate of Prostaglandin Synthesis in the mouth, and the ability to resist bacterial infection, to levels of concentration many times higher than that occurring naturally, thereby enhanceing and reconstituting the Immune System Response to effectively control, combat and destroy bacteria found in the mouth that cause dental plaque buildup that results in Caries formation, Calculus and Periodontal disease Gingivitis and Periodontitis.

2. A composition as in claim 1., wherein the amount of Pure White Phenolphthalein is 800 Mgs. dissolved in 400 Milliliters of Triethanolamine and homogeneously admixed in 8 ozs. of a pharmaceutically acceptable alkaline carrier in the form of a dental rinse.

3. A composition as in claim 1., wherein the dental rinse formulation comprises an alkaline solution with a pH of about 7.5 or above which includes homogeneously admixed in liquid carrier Pure White Phenolphthalein dissolved in Triethanolamine and additional ingredients including Sodium Salicylate or Allantoin(Glyoxyl diuride) may be optionally included as healing agents as well as optional adjuvant ingredients effective to provide desirable flavoring and coloring.

4. A method for controlling, combatting and destroying bacteria found in the mouth that cause dental plaque, and for controlling, combatting and destroying bacteria found in the mouth that cause dental plaque, and for preventing dental plaque buildup preventing dental plaque buildup, comprising rinsing the teeth surfaces and gums with the composition consisting of Pure White Phenolphthalein dissolved in Triethanolamine and homogeneously admixed in a pharmaceutically acceptable alkaline carrier in the form of a dental rinse, which when applied in the mouth as a rinse stimulates and increases the rate of Prostaglandin Synthesis in the mouth to levels of concentration many times higher than that occurring naturally, thereby enhanceing and reconstituting the Immune System Response to effectively control, combat and destroy bacteria found in the mouth that cause dental plaque buildup that results in Caries formation, Calculus and Periodontal disease Gingivitis and Periodontitis.

5. A method as in claim 4., wherein the amount of Pure White Phenolphthalein is 800 Milligrams dissolved in 400 Milliliters of Triethanolamine and homogeneously admixed in 8 ounces of a pharmaceutically acceptable alkaline carrier in the form of a dental rinse.

6. A method as in claim 4., wherein the dental rinse formulation comprises an alkaline solution with a pH of about 7.5 or above which includes homogeneously admixed in liquid carrier Pure White Phenolphthalein dissolved in Triethanolamine and additional ingredients including Sodium Salicylate or Allantoin may be optionally included as healing agents as well as optional adjuvant ingredients effective to provide desirable flavoring and coloring.

7. The method according to claim 4., wherein said rinsing is carried out once a day over a five day period, said method being effective over the five day period in preventing new plaque formation on at least about fifty percent (50%) of the dental surface area.

8. The method according to claim 4., wherein said rinsing is carried out once a day over a five day period, said composition being effective over the five day period in preventing new plaque formation on at least about fifty percent (50%) of the dental surface area.

9. A composition as in claim 1, wherein the Pure White Phenolphthalein dissolved in Triethanolamine and homogeneously admixed in a pharmaceutically acceptable alkaline carrier may be in the form of a conventional toothpaste.

* * * * *